(12) United States Patent
Stalker et al.

(10) Patent No.: US 8,676,349 B2
(45) Date of Patent: Mar. 18, 2014

(54) MECHANISM FOR RELEASABLY ENGAGING AN IMPLANTABLE MEDICAL DEVICE FOR IMPLANTATION

(75) Inventors: Kent C. B. Stalker, San Marcos, CA (US); Peter J. D'Aquanni, Murrieta, CA (US); Eric T. Johnson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1950 days.

(21) Appl. No.: 11/855,501

(22) Filed: Sep. 14, 2007

(65) Prior Publication Data
US 2008/0071339 A1   Mar. 20, 2008

Related U.S. Application Data

(60) Provisional application No. 60/844,948, filed on Sep. 15, 2006.

(51) Int. Cl.
*A61N 1/05* (2006.01)
(52) U.S. Cl.
USPC .......................................................... 607/119
(58) Field of Classification Search
USPC .......................................................... 607/119
See application file for complete search history.

(56) References Cited

U.S. PATENT DOCUMENTS

| | | |
|---|---|---|
| 3,874,388 A | 4/1975 | King et al. |
| 4,391,124 A | 7/1983 | Drost et al. |
| 4,407,296 A | 10/1983 | Anderson |
| 4,485,813 A | 12/1984 | Anderson et al. |
| 4,492,107 A | 1/1985 | Sandhu |
| 4,672,976 A | 6/1987 | Kroll |
| 4,836,204 A | 6/1989 | Landymore et al. |
| 4,846,191 A | 7/1989 | Brockway et al. |
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |

(Continued)

FOREIGN PATENT DOCUMENTS

| | | |
|---|---|---|
| EP | 0897690 | 2/1999 |
| EP | 0928598 | 8/2000 |

(Continued)

OTHER PUBLICATIONS

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

(Continued)

*Primary Examiner* — Christopher D Koharski
*Assistant Examiner* — Jeremiah Kimball
(74) *Attorney, Agent, or Firm* — Faegre Baker Daniels LLP

(57) ABSTRACT

An apparatus for releasably engaging an implantable medical device during delivery includes an elongate, tubular body having an open distal end a plurality of deflectable jaw members extending distally from the distal end of the body and terminating in distal tip portions, and an actuating member slidably disposed within the body and including a distal end portion operable to prevent inward deflection of the jaw members when positioned proximate the distal tip portions. The jaw members are adapted to releasably engage an engagement feature of the implantable medical device.

19 Claims, 12 Drawing Sheets

(56) References Cited

U.S. PATENT DOCUMENTS

| | | | |
|---|---|---|---|
| 5,218,965 A | 6/1993 | Ring | |
| 5,284,138 A | 2/1994 | Kujawski | |
| 5,303,207 A | 4/1994 | Brady et al. | |
| 5,334,217 A | 8/1994 | Das | |
| 5,411,551 A | 5/1995 | Winston et al. | |
| 5,415,630 A | 5/1995 | Gory et al. | |
| 5,451,235 A | 9/1995 | Lock et al. | |
| 5,604,531 A | 2/1997 | Iddan et al. | |
| 5,634,936 A | 6/1997 | Linden et al. | |
| 5,656,036 A | 8/1997 | Palmaz | |
| 5,662,711 A | 9/1997 | Douglas | |
| 5,704,352 A | 1/1998 | Tremblay et al. | |
| 5,725,552 A | 3/1998 | Kotula et al. | |
| 5,733,313 A | 3/1998 | Barreras, Sr. et al. | |
| 5,772,669 A | 6/1998 | Vrba | |
| 5,775,331 A | 7/1998 | Raymond et al. | |
| 5,800,497 A | 9/1998 | Bakels et al. | |
| 5,824,053 A | 10/1998 | Khosravi et al. | |
| 5,833,603 A | 11/1998 | Kovacs et al. | |
| 5,855,563 A | 1/1999 | Kaplan et al. | |
| 5,860,923 A | 1/1999 | Lenker et al. | |
| 5,891,154 A | 4/1999 | Loeffler | |
| 5,967,980 A | 10/1999 | Ferre et al. | |
| 5,967,986 A | 10/1999 | Cimochowski | |
| 5,967,989 A | 10/1999 | Cimochowski et al. | |
| 5,995,876 A | 11/1999 | Kruse et al. | |
| 6,002,969 A | 12/1999 | Machek et al. | |
| 6,015,386 A | 1/2000 | Kensey et al. | |
| 6,015,387 A | 1/2000 | Schwartz et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,077,227 A | 6/2000 | Miesel et al. | |
| 6,097,984 A | 8/2000 | Douglas | |
| 6,106,464 A | 8/2000 | Bass et al. | |
| 6,140,740 A | 10/2000 | Porat et al. | |
| 6,159,156 A | 12/2000 | Van Bockel | |
| 6,179,858 B1 | 1/2001 | Squire et al. | |
| 6,193,745 B1 | 2/2001 | Fogarty et al. | |
| 6,214,025 B1 | 4/2001 | Thistle et al. | |
| 6,231,516 B1 | 5/2001 | Keilman et al. | |
| 6,236,889 B1 | 5/2001 | Soykan et al. | |
| 6,239,724 B1 | 5/2001 | Doron et al. | |
| 6,240,312 B1 | 5/2001 | Alfano et al. | |
| 6,246,898 B1 | 6/2001 | Vesely et al. | |
| 6,277,078 B1 | 8/2001 | Porat et al. | |
| 6,278,790 B1 | 8/2001 | Davis et al. | |
| 6,309,350 B1 | 10/2001 | Van Tassel | |
| 6,328,699 B1 | 12/2001 | Eigler et al. | |
| 6,331,163 B1 | 12/2001 | Kaplan | |
| 6,379,308 B1 | 4/2002 | Brockway et al. | |
| 6,409,674 B1 | 6/2002 | Brockway et al. | |
| 6,416,474 B1 | 7/2002 | Penner et al. | |
| 6,432,050 B1 | 8/2002 | Porat et al. | |
| 6,442,413 B1 | 8/2002 | Silver | |
| 6,447,522 B2 | 9/2002 | Gambale et al. | |
| 6,475,170 B1 | 11/2002 | Doron et al. | |
| 6,486,588 B2 | 11/2002 | Doron et al. | |
| 6,527,780 B1 | 3/2003 | Wallace et al. | |
| 6,543,272 B1 | 4/2003 | Vitek | |
| 6,585,763 B1 | 7/2003 | Keilman et al. | |
| 6,592,553 B2 | 7/2003 | Zhang et al. | |
| 6,628,989 B1 | 9/2003 | Penner et al. | |
| 6,645,143 B2 | 11/2003 | Van Tassel et al. | |
| 6,660,021 B1 | 12/2003 | Palmer et al. | |
| 6,685,638 B1 | 2/2004 | Taylor et al. | |
| 6,689,056 B1 * | 2/2004 | Kilcoyne et al. | 600/300 |
| 6,699,186 B1 | 3/2004 | Wolinsky et al. | |
| 6,702,847 B2 | 3/2004 | DiCarlo | |
| 6,730,108 B2 | 5/2004 | Van Tassel et al. | |
| 6,738,671 B2 | 5/2004 | Christophersom et al. | |
| 6,743,173 B2 | 6/2004 | Penner et al. | |
| 6,746,404 B2 | 6/2004 | Schwartz | |
| 6,747,916 B1 | 6/2004 | Fluery et al. | |
| 6,755,855 B2 | 6/2004 | Yurek et al. | |
| 6,764,446 B2 | 7/2004 | Wolinsky et al. | |
| 6,783,499 B2 | 8/2004 | Schwartz | |
| 6,800,060 B2 | 10/2004 | Marshall | |
| 6,840,956 B1 | 1/2005 | Wolinsky et al. | |
| 6,855,115 B2 | 2/2005 | Fonseca et al. | |
| 6,868,288 B2 | 3/2005 | Thompson | |
| 6,890,303 B2 | 5/2005 | Fitz | |
| 6,899,729 B1 | 5/2005 | Cox | |
| 6,904,308 B2 | 6/2005 | Frisch et al. | |
| 6,920,347 B2 | 7/2005 | Simon et al. | |
| 6,926,670 B2 | 8/2005 | Rich | |
| 6,934,573 B1 | 8/2005 | Glukhovsky et al. | |
| 6,950,690 B1 | 9/2005 | Meron et al. | |
| 6,958,034 B2 | 10/2005 | Iddan | |
| 6,970,742 B2 | 11/2005 | Mann et al. | |
| 6,972,017 B2 | 12/2005 | Smith et al. | |
| 6,984,205 B2 | 1/2006 | Gazdzinski | |
| 7,001,329 B2 | 2/2006 | Kobayashi et al. | |
| 7,006,858 B2 | 2/2006 | Silver et al. | |
| 7,009,634 B2 | 3/2006 | Iddan et al. | |
| 7,011,671 B2 | 3/2006 | Welch | |
| 7,024,248 B2 | 4/2006 | Penner et al. | |
| 7,033,322 B2 | 4/2006 | Silver | |
| 7,035,684 B2 | 4/2006 | Lee | |
| 7,039,453 B2 | 5/2006 | Mullick et al. | |
| 7,060,038 B2 | 6/2006 | Letort et al. | |
| 7,064,472 B2 | 6/2006 | Peline et al. | |
| 7,065,409 B2 | 6/2006 | Mazar | |
| 7,076,305 B2 | 7/2006 | Imran et al. | |
| 7,083,822 B2 | 8/2006 | Brightbill | |
| 7,116,352 B2 | 10/2006 | Yaron | |
| 7,118,529 B2 | 10/2006 | Glukhovsky et al. | |
| 7,118,531 B2 | 10/2006 | Krill | |
| 7,131,986 B2 | 11/2006 | Sirhan et al. | |
| 7,160,258 B2 | 1/2007 | Imran et al. | |
| 7,181,261 B2 | 2/2007 | Silver et al. | |
| 7,198,603 B2 | 4/2007 | Penner et al. | |
| 7,211,045 B2 | 5/2007 | Dala-Krishna et al. | |
| 7,273,457 B2 | 9/2007 | Penner | |
| 7,283,874 B2 | 10/2007 | Penner | |
| 7,308,319 B2 | 12/2007 | Lovett et al. | |
| 7,338,512 B2 | 3/2008 | McGuckin, Jr. et al. | |
| 7,347,868 B2 | 3/2008 | Burnett et al. | |
| 7,392,094 B2 | 6/2008 | Zhang et al. | |
| 7,437,193 B2 | 10/2008 | Parramon et al. | |
| 7,452,334 B2 | 11/2008 | Gianchandani et al. | |
| 7,477,946 B2 | 1/2009 | Tockman et al. | |
| 7,555,351 B2 | 6/2009 | Zhang et al. | |
| 7,744,542 B2 | 6/2010 | Piaget et al. | |
| 7,780,694 B2 | 8/2010 | Palmer et al. | |
| 7,801,626 B2 * | 9/2010 | Moser | 607/126 |
| 7,850,708 B2 | 12/2010 | Pal | |
| 7,890,188 B2 | 2/2011 | Zhang et al. | |
| 2002/0045920 A1 | 4/2002 | Thompson | |
| 2002/0123672 A1 | 9/2002 | Christophersom et al. | |
| 2002/0165601 A1 | 11/2002 | Clerc | |
| 2002/0183628 A1 | 12/2002 | Reich et al. | |
| 2002/188207 A1 | 12/2002 | Richter | |
| 2003/0114897 A1 | 6/2003 | Von Arx et al. | |
| 2003/0139796 A1 | 7/2003 | Sequin et al. | |
| 2003/0200031 A1 | 10/2003 | de Kok | |
| 2004/0006377 A1 | 1/2004 | Behm | |
| 2004/0116992 A1 | 6/2004 | Wardle et al. | |
| 2004/0147969 A1 | 7/2004 | Mann et al. | |
| 2004/0176672 A1 | 9/2004 | Silver et al. | |
| 2004/0204744 A1 | 10/2004 | Penner et al. | |
| 2004/0215228 A1 | 10/2004 | Simpson et al. | |
| 2005/0080472 A1 | 4/2005 | Atkinson et al. | |
| 2005/0096702 A1 | 5/2005 | Denker et al. | |
| 2005/0115561 A1 | 6/2005 | Stahmann et al. | |
| 2005/0124875 A1 | 6/2005 | Kawano et al. | |
| 2005/0136385 A1 | 6/2005 | Mann et al. | |
| 2005/0149108 A1 | 7/2005 | Cox | |
| 2005/0149128 A1 | 7/2005 | Heil, Jr. et al. | |
| 2005/0149155 A1 | 7/2005 | Scheiner et al. | |
| 2005/0149156 A1 | 7/2005 | Libbus et al. | |
| 2005/0154321 A1 | 7/2005 | Wolinsky et al. | |
| 2005/0165456 A1 | 7/2005 | Mann et al. | |

(56) References Cited

U.S. PATENT DOCUMENTS

| | | |
|---|---|---|
| 2005/0209678 A1 | 9/2005 | Henkes et al. |
| 2005/0245840 A1 | 11/2005 | Christopherson et al. |
| 2006/0009818 A1 | 1/2006 | Von Arx et al. |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0079740 A1 | 4/2006 | Silver et al. |
| 2006/0089627 A1 | 4/2006 | Burnett et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142819 A1 | 6/2006 | Penner et al. |
| 2006/0149329 A1 | 7/2006 | Penner |
| 2006/0149330 A1 | 7/2006 | Mann et al. |
| 2006/0178586 A1 | 8/2006 | Dobak, III |
| 2006/0206153 A1 | 9/2006 | Libbus et al. |
| 2006/0241735 A1 | 10/2006 | Tockman et al. |
| 2006/0259085 A1 | 11/2006 | Zhang et al. |
| 2006/0287700 A1 | 12/2006 | White et al. |
| 2006/0293741 A1 | 12/2006 | Johnson et al. |
| 2007/0049833 A1 | 3/2007 | Tearney et al. |
| 2007/0129637 A1 | 6/2007 | Wolinsky et al. |
| 2007/0156126 A1 | 7/2007 | Flaherty |
| 2007/0156205 A1 | 7/2007 | Larson et al. |
| 2007/0162090 A1 | 7/2007 | Penner |
| 2007/0179583 A1 | 8/2007 | Goetzinger et al. |
| 2007/0191904 A1 | 8/2007 | Libbus et al. |
| 2007/0208390 A1 | 9/2007 | Von Arx et al. |
| 2007/0250126 A1 | 10/2007 | Maile et al. |
| 2007/0274565 A1 | 11/2007 | Penner |
| 2007/0282413 A1 | 12/2007 | Tockman et al. |
| 2007/0282415 A1 | 12/2007 | Tockman et al. |
| 2008/0071178 A1 | 3/2008 | Greenland et al. |
| 2008/0071248 A1 | 3/2008 | Delgado et al. |
| 2008/0108904 A1 | 5/2008 | Heil |
| 2008/0176271 A1 | 7/2008 | Silver et al. |
| 2008/0275350 A1 | 11/2008 | Liao et al. |
| 2008/0283066 A1 | 11/2008 | Delgado et al. |
| 2009/0054793 A1 | 2/2009 | Nunez et al. |
| 2009/0171274 A1 | 7/2009 | Harlev et al. |
| 2009/0270742 A1 | 10/2009 | Wolinsky et al. |
| 2010/0016840 A1 | 1/2010 | Stahmann et al. |
| 2010/0210923 A1 | 8/2010 | Li et al. |

FOREIGN PATENT DOCUMENTS

| | | |
|---|---|---|
| EP | 1068836 | 1/2001 |
| EP | 1488735 | 6/2007 |
| GB | 2333044 | 7/1999 |
| JP | H(11)-089942 | 4/1999 |
| JP | 2000-507142 | 6/2000 |
| JP | 2001-061790 | 3/2001 |
| JP | 2006-500991 | 1/2006 |
| WO | WO83/03348 | 10/1983 |
| WO | WO99/34731 | 7/1999 |
| WO | WO00/16686 | 3/2000 |
| WO | WO2000/059376 | 10/2000 |
| WO | 0167989 | 9/2001 |
| WO | WO01/87137 | 11/2001 |
| WO | WO 2004/024034 | 3/2004 |
| WO | WO 2004/110263 | 12/2004 |
| WO | WO 2005/058202 | 6/2005 |
| WO | WO2005/067817 | 7/2005 |
| WO | WO2007/057739 | 5/2007 |
| WO | WO 2007/062299 | 5/2007 |
| WO | WO2007/082115 | 7/2007 |
| WO | WO 2008/002654 | 1/2008 |
| WO | WO2008/034077 | 3/2008 |
| WO | WO2008/057720 | 5/2008 |
| WO | WO2008/060197 | 5/2008 |
| WO | WO2008/144191 | 11/2008 |
| WO | WO 2009/006610 | 1/2009 |

OTHER PUBLICATIONS

International Search Report and Written Opinion from PCT/US2008/062229, mailed Jan. 5, 2009.

Goodall, Eleanor V. et al., "Position-Selective Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

International Search Report and Written Opinion issued in PCT/US2010/020756, mailed Sep. 27, 2010.

Invitation to Pay Fees and Partial Search Report issued in PCT/US2010/020756, mailed May 12, 2010.

Holmes et al. "SirolimusEluting Stents vs. Vascular Brachytherapy for InStent Restenosis Within Bare-Metal Stents" JAMA295 (11): 12641273 Mar. 15, 2006.

Sheth et al. "Subacute Thrombosis and Vascular Injury Resulting From Slotted-Tube Nitinol and Stainless Steel Stents in a Rabbit Carotid Artery Model" Circulation 94: 17331740.

Stone et al. "Paclitaxel-Eluting Stents vs. Vascular Brachytherapy for InStent Restenosis Within BareMetal Stents" JAMA 295( 11): 12531263.

Webster's II new Riverside University Dictionary, Riverside Publishing Company, 1994, pp. 421 and 625.

Wenaweser et al. "Stent thrombosis following bare-metal stent implantation: success of emergency percutaneous coronary intervention and predictors of adverse outcome" European Heart Journal 26: 11801187 2005.

International Search Report and Written Opinion of international application No. PCT/US20051041989, dated Apr. 25, 2006.

\* cited by examiner

MECHANISM FOR RELEASABLY ENGAGING AN IMPLANTABLE MEDICAL DEVICE FOR IMPLANTATION

CROSS REFERENCE TO RELATED APPLICATION

The present application claims priority under 35 U.S.C. §119 to U.S. Provisional Application Ser. No. 60/844,948, filed Sep. 15, 2006, entitled "MECHANISM FOR RELEASABLY ENGAGING AN IMPLANTABLE MEDICAL DEVICE FOR IMPLANTATION" which is incorporated herein by reference in its entirety.

TECHNICAL FIELD

The present invention relates to medical devices and methods for anchoring implantable medical devices in the body. In particular, the present invention is a mechanism for use with a delivery system for releasably engaging an implantable medical device during delivery and deployment.

BACKGROUND

Medical devices are known that can be implanted within a patient's body for monitoring one or more physiological parameters and/or for providing therapeutic functions. For example, sensors or transducers can be placed in the body for monitoring a variety of properties, such as temperature, blood pressure, strain, fluid flow, chemical properties, electrical properties, magnetic properties, and the like. In addition, medical devices can be implanted that perform one or more therapeutic functions, such as drug delivery, cardiac pacing, defibrillation, electrical stimulation, and the like.

One parameter of particular interest is blood pressure. One or more implantable pressure sensing modules can be used in conjunction with cardiac rhythm management (CRM) devices to facilitate optimization of CRM device settings. In such systems, the pressure sensing module is delivered transvenously to a target vessel (e.g., the pulmonary artery) and anchored in the vessel using various fixation techniques. Accurate placement of the sensing module is an important factor in accurately and reliably measuring the desired parameter. Additionally, under some circumstances, it becomes necessary to re-position an implantable sensor module after initial deployment or, alternatively, to remove the sensor from the patient entirely.

Thus, a need exists for apparatus and methods for accurately delivering and deploying implantable medical devices within a patient's body. In particular, there is a need for a mechanism for releasably engaging an implantable sensor to facilitate accurate deployment of the sensor at a desired implantation site.

SUMMARY

The present invention, in one embodiment, is an apparatus for releasably engaging an implantable medical device during delivery, the implantable medical device including an engagement feature. The device comprises an elongate, tubular body having an open distal end, a plurality of deflectable jaw members extending distally from the distal end of the body and terminating in distal tip portions, and an actuating member slidably disposed within the body. The jaw members are adapted to releasably engage the engagement feature of the implantable medical device. The actuating member includes a distal end portion operable to prevent inward deflection of the jaw members when positioned proximate the distal tip portions.

In another embodiment, the present invention is a system comprising an elongate catheter having an inner lumen, an implantable sensor sized to be slidably received within the lumen, the sensor having a proximal portion including an engagement feature, and a retaining element movable within the lumen. The retaining element includes an elongate, tubular body having an open distal end, a plurality of deflectable jaw members extending distally from the distal end of the body and terminating in distal tip portions, and an actuating member slidably disposed within the body. The jaw members are adapted to releasably engage the engagement feature of the implantable medical device. The actuating member includes a distal end portion operable to prevent inward deflection of the jaw members when positioned proximate the distal tip portions.

In yet another embodiment, the present invention is a method for delivering an implantable medical device including an aperture. The method comprises releasably engaging the implantable medical device by inserting jaw members of a retaining element through the aperture in the implantable medical device such that the jaw members engage an inner surface of the aperture, the jaw members extending distally from an elongate, tubular body of the retaining element. The method includes next advancing an actuating member through the body and positioning a distal end portion of the actuating member at a location proximate the distal tip portions of the jaw members to prevent inward deflection of the jaw members. The method further includes next positioning the implantable medical device as desired, retracting the actuating member to a location proximal to the jaw members, and retracting the body relative to the implantable medical device to retract the jaw members from the aperture.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
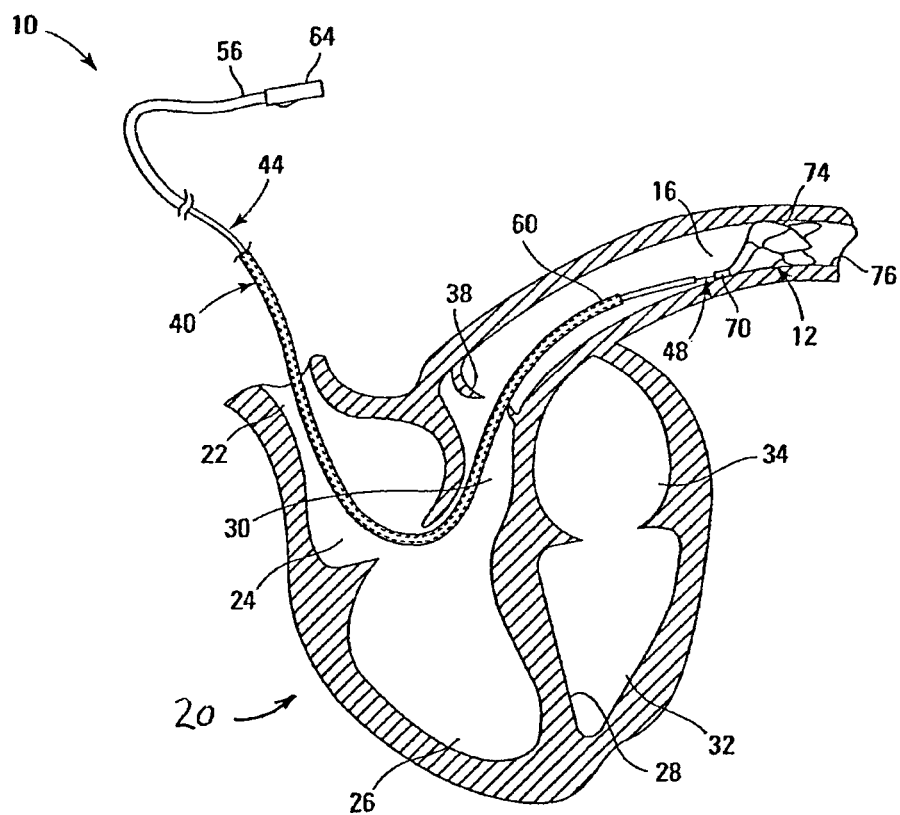
FIG. 1 is a schematic view of a delivery system for delivering an implantable medical device, which in the illustrated embodiment is an implantable sensor assembly, to an implantation site within a pulmonary artery of a heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a delivery system 10 for delivering an implantable medical device, which in the illustrated embodiment is an implantable sensor assembly 12, to a target implantation site within a pulmonary artery 16 of a heart 20 according to one embodiment of the present invention. As shown, the heart 20 generally includes a superior vena cava 22, a right atrium 24, a right ventricle 26, a ventricular septum 28, a right ventricular outflow tract 30, a left ventricle 32 and a left atrium 34. As shown, the right ventricular outflow tract 30 leads to the pulmonary artery 16, which is separated from the right ventricle by a pulmonary artery valve 38.

The delivery system 10 is sized (i.e., has a length and diameter) to navigate the patient's vasculature to the target implantation site from a location external to the patient's body. In the illustrated embodiment, the delivery system 10 enters the heart 20 through the superior vena cava 22, and extends through the right atrium 24 and the right ventricular outflow tract 30 to deliver the implantable sensor assembly 12 in the main pulmonary artery 16. In such an embodiment, the delivery system 10 may be transvenously advanced to the heart 20 by any methods known in the art. For example, as is well known, the delivery system 10 may enter the patient's vasculature system through a percutaneous incision into the left subclavian vein, the left auxiliary vein, the left internal or external jugular vein, the left brachiocephalic vein, or through a femoral approach. In various embodiments, the delivery system 10 may be used to deliver an implantable sensor assembly 12 to a branch of the pulmonary artery 16 (e.g., the right or left pulmonary artery, not shown). In other embodiments, the delivery system 10 may be used to deliver an implantable sensor assembly to other areas of the patient's vasculature.

As shown in FIG. 1, the delivery system 10 includes a flexible, elongate outer catheter 40, a flexible, elongate inner member 44 disposed within the outer catheter 40, and a flexible, elongate retaining element 48 disposed within the inner member 44 and releasably engaged with the sensor assembly 12. The outer catheter includes a proximal end 56 and a distal end 60. As will be appreciated, the outer catheter 40 includes at least one lumen (not shown in FIG. 1) through which the inner member 44 is disposed. As will be explained in detail below, the delivery system 10 and other embodiments of the present invention, advantageously provide accurate control over the implantation location of the sensor assembly 12. Additionally, the delivery systems of the present invention allow the physician to re-position and re-deploy the sensor assembly 12 if necessary or desired.

The outer catheter 40 and the inner member 44 are movable relative to each other, and the retaining element 48 is movable relative to the inner member 44, to deploy the sensor assembly 12 at the target implantation site. In the illustrated embodiment, the delivery system 10 includes a control mechanism 64 on the proximal end 56 of the outer catheter 40 and which is operatively coupled to at least the inner member 44. The control mechanism 64 is operable to allow a physician to control relative movement of at least the outer catheter and inner member 40, 44, and in some embodiments, the retaining element 48, for delivery and deployment of the sensor assembly 12. The control mechanism 64 may include any mechanism or structure known or later developed for controlling the relative longitudinal and/or rotational movement of inner and outer catheters of a dual catheter system. In one exemplary embodiment, the control mechanism 64 includes a thumbwheel operatively coupled to the inner member 44 to permit the physician to slide the inner member 44 within the outer catheter 40.

The outer catheter 40 can be any catheter known in the art or later developed for accessing a target implantation location in a patient's vasculature. As will be appreciated, the particular design and construction, including materials, of the outer catheter 40 is determined based on the needs of the patient, and in particular, the selected implantation location for the implantable sensor assembly 12. In one embodiment, the outer catheter 40 is a catheter configured for accessing the pulmonary artery 16 or a branch thereof. In one embodiment, the outer catheter 40 can be advanced to the pulmonary artery 16 over a guidewire positioned therein through a Swan Ganz procedure, in which a balloon catheter is inserted into the venous system and floated with the blood flow into and through the heart 20 out to the pulmonary artery 16.

As shown in FIG. 1, the sensor assembly 12 includes an implantable sensor 70 and an anchor 74 coupled to the sensor 70. As will be discussed in more detail below, the anchor 74 is an expandable structure configured to assume a collapsed configuration for transvenous delivery of the sensor assembly 12 to the desired implantation location through the delivery system 10, and an expanded configuration, illustrated in FIG. 1, in which the anchor 74 engages an inner surface 76 of the pulmonary artery 16.

The sensor 70 may be configured to perform one or more designated functions, which may include taking one or more physiological measurements. The sensor 70 may be configured to measure any known physiologic parameters such as, for example, blood pressure, temperature, blood or fluid flow, strain, electrical, chemical, or magnetic properties within the body. The specific parameters to be measured, and thus the implantation site for the sensor assembly 12, are determined based on the particular therapeutic needs of the patient. In one exemplary embodiment, the sensor 70 may be configured to measure blood pressure in the pulmonary artery 16 (e.g., as illustrated in FIG. 1). In one embodiment, the sensor 70 may further be adapted to store and/or transmit blood pressure data to another implanted device (e.g., a cardiac rhythm management device such as a pacemaker, not shown) and/or a device (e.g., a monitor or programmer) located external to the patient's body.

In various embodiments, the sensor 70 is configured to communicate with other devices, such as an external device or another implantable medical device (e.g., a pacemaker and/or defibrillator) via a wireless communication link. Various types of wireless communication circuitry are well known in the art, and the specific type and/or style of wireless communication that can be used is not limited. For example, ultrasonic waves, acoustic communications, radio frequency communications, and the like may be used. In one embodiment, the sensor 70 includes an acoustic transmitter/receiver configured for acoustic telemetry.

Figure 2:
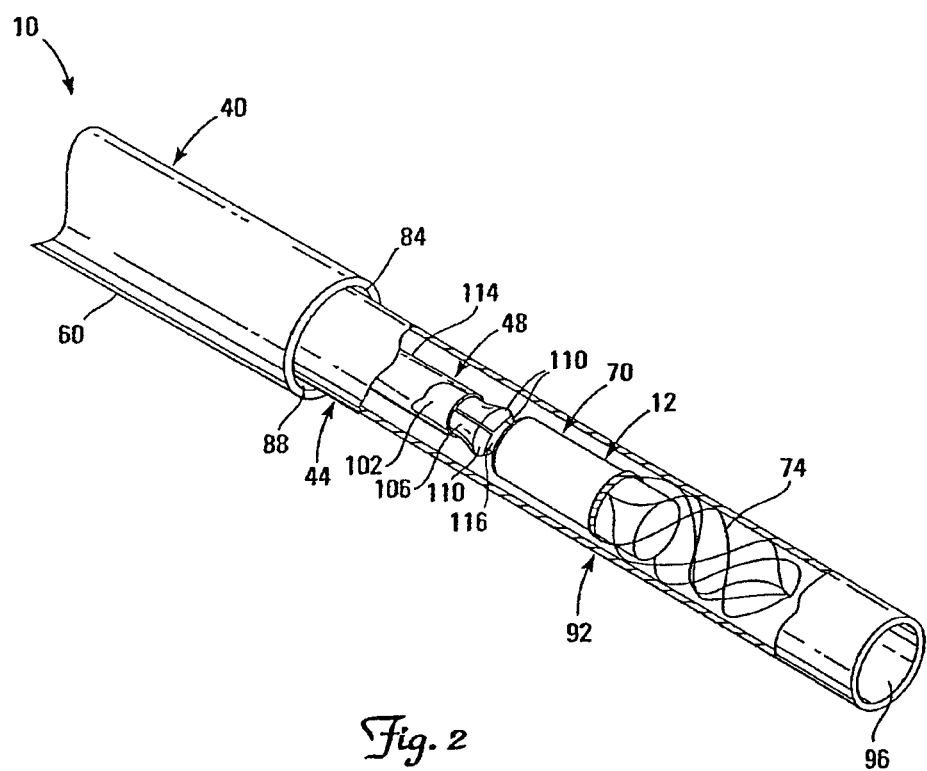
FIG. 2 is a partial cutaway perspective view of the distal portion of the delivery system of FIG. 1.

FIG. 2 is a perspective view of the distal portion of the delivery system 10 showing a partial cutaway of the inner member 44, and further showing the implantable sensor assembly 12 releasably coupled to the retaining element 48 for delivery of the sensor assembly 12. As shown in FIG. 2, the outer catheter 40 includes a lumen 84 sized to slidably receive the inner member 44, and terminates in a distal opening 88. As further shown in FIG. 2, the inner member 44 includes a distal end portion 92 in the form of a sheath having a distal opening 96 and an inner diameter and length sized to receive the sensor assembly 12 so as to maintain the anchor 74 of the sensor assembly 12 in a collapsed configuration during delivery.

As can further be seen in FIG. 2, the retaining element 48 includes a body 102 having a distal end 106, a plurality of deflectable jaw members 110 extending distally from the distal end 106, and a tubular actuating member 114 (shown in cutaway view to illustrate the body 102) slidably disposed over the body 102. The jaw members 110 operate as a sensor engagement structure for releasably engaging a portion of the sensor 70. As will be explained in more detail below, the jaw members 110 are naturally biased radially outwardly in an undeflected state, and the actuating member 114 is configured to force the jaw members 110 radially inward so as to engage the sensor assembly 12 by clamping onto the sensor assembly 12.

In the illustrated embodiment, the sensor 70 includes a hub 116 at its proximal end. As shown, the hub 116 is configured to mate with the jaw member 110 to promote positive coupling of the retaining element 48 and the sensor 70. In other embodiments, a different engagement feature may be included on the sensor 12. In other embodiments, the hub 116 or other engagement feature may be omitted.

In various embodiments, the retaining element 48 may include different sensor engagement structures. For example, in one embodiment, the retaining element 48 may include an elongated tether having a hook at its distal end, which hook is adapted to engage an aperture or loop on the sensor 70. Other embodiments may incorporate still other sensor engagement structures. In still other embodiments, the retaining element 48 is simply a solid or tubular structure (i.e., lacks the jaw members 110 and actuating member 114), and can be used to push the sensor assembly 12 distally and/or resist proximal displacement of the sensor assembly 12.

The inner member 44 and the retaining element 48 are dimensioned so as to extend proximally from the implantation location (e.g., a location within the pulmonary artery 16 as shown in FIG. 1) to or near the proximal end 56 of the outer catheter 40. Additionally, as shown in FIG. 2, the outer catheter 40 can be retracted proximally relative to the inner member 40, or alternatively, the inner member 44 (with the sensor assembly 12 retained therein) can be advanced distally relative to the outer catheter 40, such that the sensor assembly 12 may be deployed from the distal opening 96 of the inner member 40 without interference from the outer catheter 40.

The outer catheter 40 is sized to accommodate the selected implantable sensor assembly 12 (or other implantable device), and as will be appreciated, has a length sufficient to transvenously deliver the sensor assembly 12 to the desired implantation site through a percutaneous access site such as described above. In various exemplary embodiments, the outer catheter 40 may range in size from a 6 French to a 20 French guide catheter. In some embodiments, for example, where the sensor assembly 12 is configured for implantation in the pulmonary artery 16, the outer catheter 40 may range in size from 10 French to 16 French.

The inner member 44 may be made from substantially the same or identical materials as the outer catheter 40. In some embodiments, the inner member 44 may be made substantially from a braided composite tubing as is known in the art for catheters and the like. In some embodiments, the distal end portion 92 of the inner member 44 may be made from a relatively low durometer material such as, for example, low-durometer Pebax. In other embodiments, the inner surface of the distal end portion 92 may include a biocompatible, lubricious coating to facilitate relative displacement of the inner member 44 and the sensor assembly 12 without undue friction.

The materials selected for the retaining element 48 are not of particular significance. In some embodiments, the body 102 and/or the actuating member 114 may be made from a metal (e.g., stainless steel) or a polymeric material. In some embodiments, the jaw members 110 may be made from materials exhibiting shape memory and/or superelastic properties, such as, for example, Nitinol or any of a number of other shape memory alloys or polymers. In some embodiments, the retaining element 48 may include a radio-opaque marker at or near its distal end.

Figure 3:
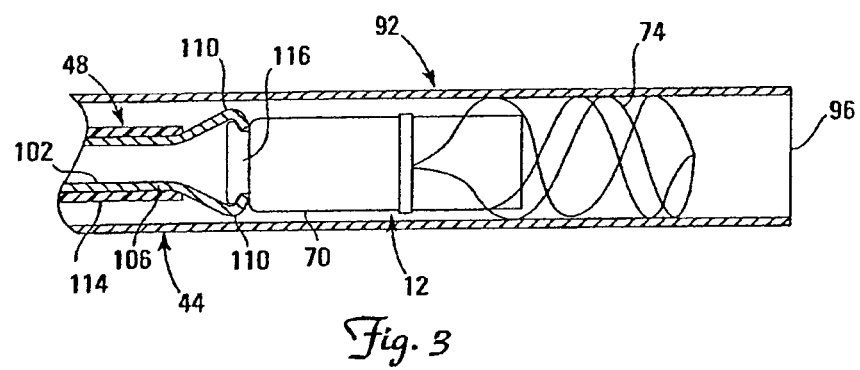
FIGS. 3-5 are partial cross-sectional views of the distal portions of an inner member and a retaining element of the delivery system of FIG. 1.
Figure 4:
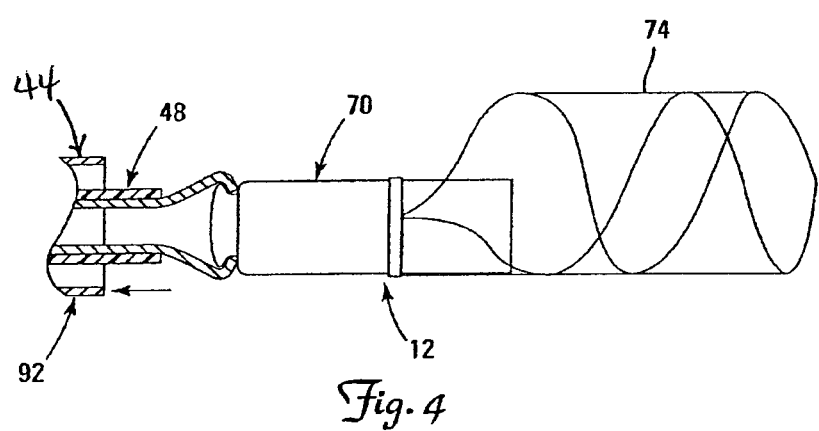
Figure 5:
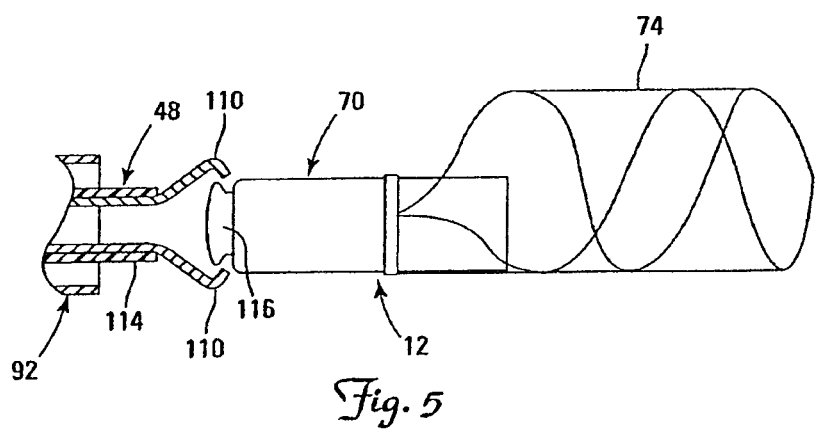

FIGS. 3-5 are partial cross-sectional views of the distal portions of the inner member 44 and the retaining element 48 illustrating the deployment of the sensor assembly 12 from the inner member 44 according to one embodiment of the present invention. It will be appreciated that the outer catheter 40 has already been retracted proximally relative to the inner member 44, such as is shown in FIG. 2. As shown in FIG. 3, the sensor assembly 12 is initially fully retained within the distal end portion 92 of the inner member 40, with the anchor 74 in the collapsed configuration. As further shown in FIG. 3, the actuating member 114 of the retaining element 48 is positioned at least partially over the jaw members 110, thereby clamping the jaw members 110 onto the proximal hub 116 of the sensor 70. As explained above, however, in other embodiments, the jaw members 110 may engage other engagement features of the sensor assembly 12. Alternatively, the engagement feature may be omitted, and the jaw members may engage other portions of the sensor assembly 12 (e.g., the housing of the sensor 70 or a portion of the anchor 74).

In FIG. 4, the inner member 44 has been moved proximally relative to the sensor assembly 12 so as to release the sensor assembly 12 (or at a minimum, the anchor 74) from the distal end portion 92 of the inner member 44. With the inner member 44 so positioned, the anchor 74 is permitted to expand to an expanded configuration for frictionally engaging an inner surface of the target vessel (e.g., the pulmonary artery, see FIG. 1) to secure the sensor assembly 12 therein. The anchor 74 may be a self-expanding anchor having a stent-like structure similar to known cardiovascular stents. Alternatively, the anchor 74 may be expandable by other means (e.g., by a balloon). In various embodiments, the anchor 74 may be any of the anchoring structures disclosed in co-pending and commonly assigned U.S. patent application Ser. No. 11/216,738 entitled "DEVICES AND METHODS FOR POSITIONING AND ANCHORING IMPLANTABLE SENSOR DEVICES" filed Aug. 31, 2005, and U.S. Provisional Patent Application Ser. No. 60/844,821 entitled "ANCHOR FOR AN IMPLANTABLE SENSOR" filed Sep. 15, 2006. The contents of the foregoing pending applications are incorporated herein by reference for all purposes.

As shown in FIG. 4, the retaining element 48 can remain coupled to the sensor assembly 12 after deployment of the anchor 74 from the distal end portion 92 of the inner member 44. This permits the sensor assembly 12 to be repositioned to another location within the target vessel, or another area of the patient's vasculature, if desired. For example, it may be desirable to perform various diagnostic tests on the sensor 70 to confirm that it is functioning properly and/or that the chosen implantation location is suitable. Alternatively, or additionally, the physician may wish to confirm that the sensor assembly 12 is sufficiently secured at the implantation site before releasing the retaining element 48. In particular, where the anchor 74 is one of the re-positionable anchor structures disclosed in co-pending and commonly assigned U.S. Provisional Patent Application Ser. No. 60/844,821 entitled "ANCHOR FOR AN IMPLANTABLE SENSOR", the sensor assembly 12, including the anchor 74, can be retracted within the distal end portion 92 of the inner member 44 by pulling proximally on the retaining element 48 while holding the inner member 44 in place. The inner member 44, with the sensor assembly 12 retained therein, can then be re-positioned within the target vessel, and the sensor assembly 12 re-deployed as described above. Alternatively, the inner member 44 may be retracted back within the outer catheter 40 (see FIG. 2), and the entire delivery system can be re-located to a different target implantation site, or can be removed from the patient entirely.

FIG. 5 illustrates the sensor assembly 12 after being de-coupled from the retaining element 48. As shown in FIG. 5, with the actuating member 114 retracted proximally, the jaw members 110 are allowed to resume their undeflected configuration and disengage from the hub 116.

Figure 6:
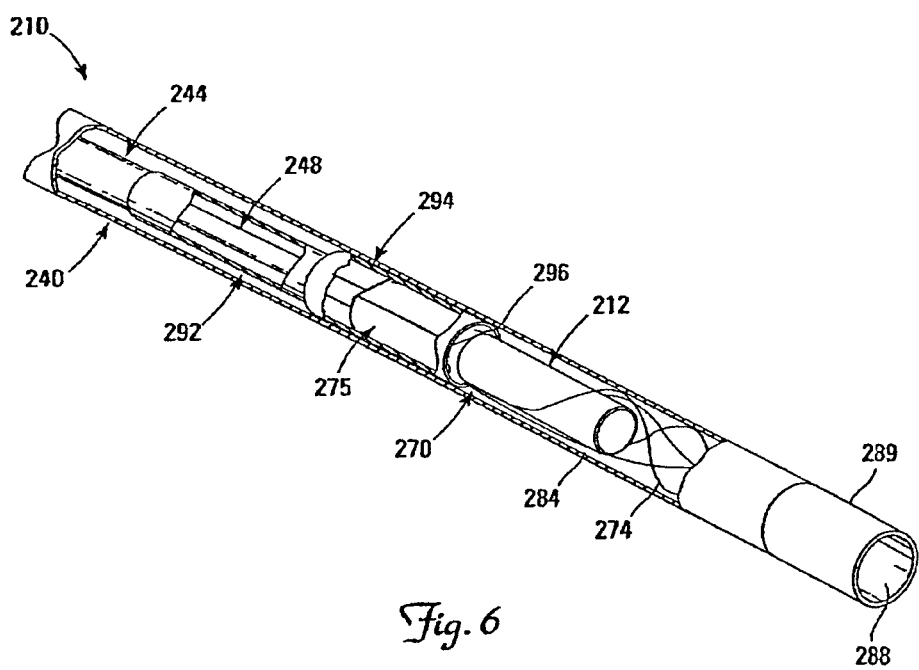
FIG. 6 is a partial cutaway view of a distal portion of an implantable sensor delivery system according to another embodiment of the present invention.

FIG. 6 is a partial cutaway view of a distal portion of an implantable sensor delivery system 210 and an implantable sensor assembly 212 coupled thereto according to another embodiment of the present invention. As shown in FIG. 6, the delivery system 210 includes an elongate outer catheter 240, an elongate inner member 244, and an elongate retaining element 248. As further shown in FIG. 6, like the sensor assembly 12 described above, the sensor assembly 212 includes a sensor element 270 and an anchor portion 274. In the illustrated embodiment, the sensor 270 includes a proximal portion 275 releasably engaged by and received by the inner member 244.

As shown, the outer catheter includes a lumen 284 sized to slidably receive the inner member 244, and terminates in a distal opening 288. The outer catheter 240 may be of substantially the same construction as the outer catheter 40 described above. In the illustrated embodiment, the outer catheter 240 includes a radio-opaque end portion 289, which may optionally include an atraumatic tip. In other embodiments, the radio-opaque portion 289 is omitted.

As further shown in FIG. 6, the inner member 244 is generally tubular and includes a distal end portion 292 including a socket 294 having a distal opening 296 and an inner diameter and length sized to receive and frictionally engage at least a portion, (i.e., in the illustrated embodiment, the proximal portion 275) of the sensor 270. Thus, unlike the distal end portion 92 of the inner member 44 described above, the distal end portion 292 is not sized to receive the entire sensor assembly 212, and in particular, the anchor portion 274 of the sensor assembly 212. Rather, in the embodiment illustrated in FIG. 6, the anchor portion 274 is retained in its collapsed configuration for delivery by the outer catheter 240. The outer catheter 240 and/or the inner member 244 may include at or near their proximal ends (not shown) a control mechanism similar or identical to those described above in connection with the delivery system 10.

In one embodiment, the sensor proximal end portion 275 may be held within the socket 294 by an interference fit. In such embodiments, the inner diameter of the socket 294 may be sized to be from about 0.002 inches to about 0.004 inches smaller than the outer diameter of the sensor proximal end portion 275, to ensure sufficient frictional engagement of the sensor 270 during delivery. In another embodiment, a relatively weak adhesive bond may be utilized to releasably retain the sensor proximal end portion 275 within the socket 294.

As shown, the retaining element 248 is disposed within the generally tubular inner member 244, and like the retaining element 48 described above, is adapted to releasably engage the sensor assembly 212. Thus, it will be appreciated that the retaining element 248 may be substantially the same or identical in design and/or function as the retaining element 48 described above. For example, in one embodiment, the retaining element 248 may have the same sensor engagement structure (e.g., deflectable jaw members) as the retaining element 48. Similarly, as will further be appreciated, the sensor 270, or in some embodiments, another portion of the sensor assembly 212, may include an engagement feature similar to the hub 116 of the sensor 70. In still other embodiments, the retaining element 248 may include no distal mechanism (such as the jaw members 110 of the retaining element 48), and may simply allow the physician to push the sensor assembly 212 distally, or alternatively, to resist proximal displacement of the sensor assembly 212. In short, any structure or mechanism capable of releasably engaging and retaining the sensor assembly 212 during delivery and deployment can be incorporated into the retaining element 248.

FIGS. 7-10 illustrate the sensor assembly 212 being deployed using the implantable sensor assembly delivery system 210 according to one embodiment of the present invention. For the purpose of this description only, the anchor 274 is not shown in FIGS. 7-10. It is emphasized that the sensor assembly 212 shown in FIGS. 7-10, however, may also include the anchor 274, which may be a self-expanding anchor similar or identical to those described above with respect to the anchor 74.

Figure 7:
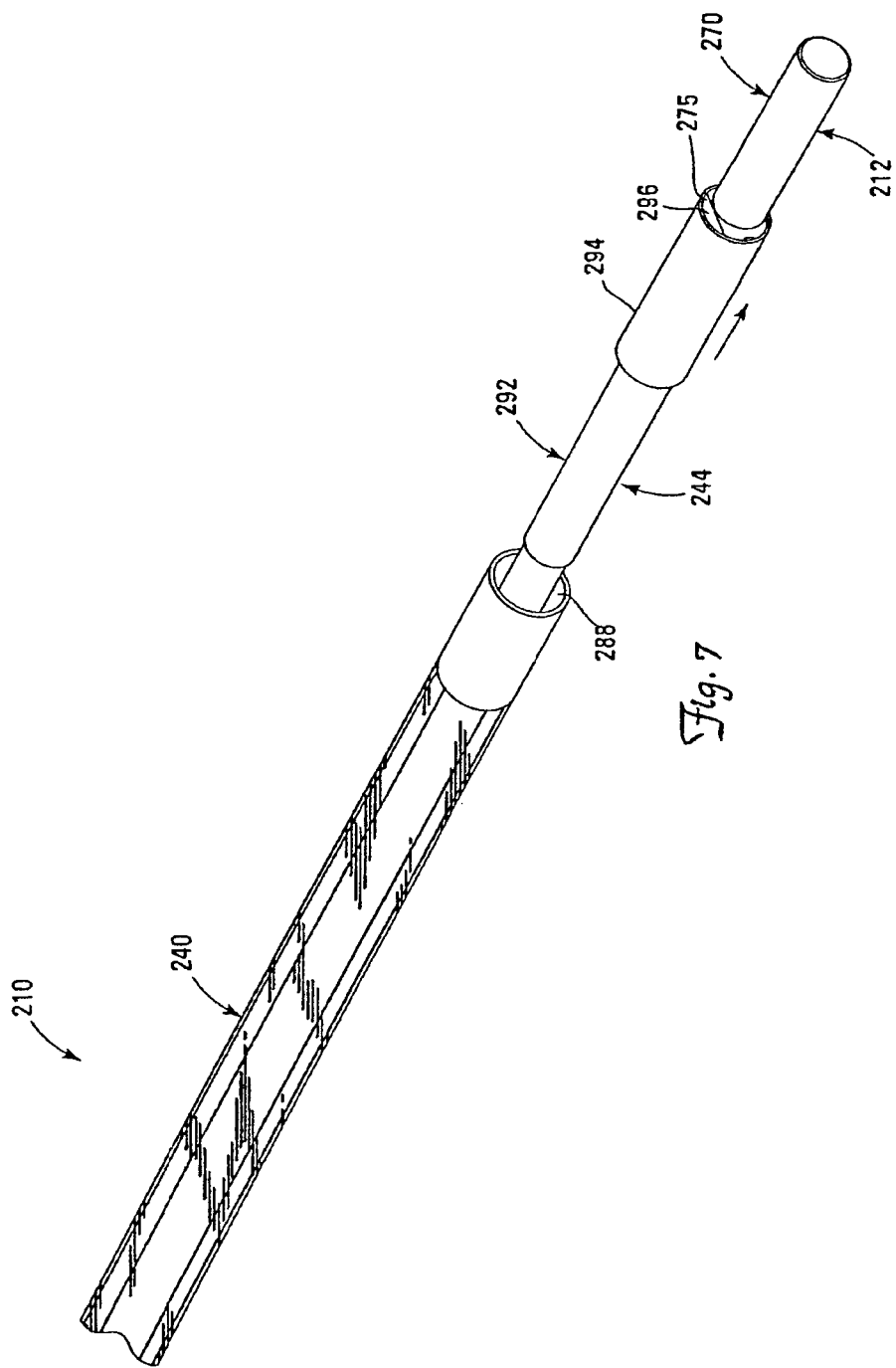
FIGS. 7-10 are perspective views illustrating a sensor assembly being deployed using the implantable sensor assembly delivery system of FIG. 6.

As shown in FIG. 7, the distal end portion 292 can be displaced distally with respect to the outer catheter 240. This can be accomplished by maintaining the outer catheter 240 in place and distally advancing the inner member 244 (e.g., by use of a control mechanism operatively coupled to one or both of the outer catheters 240 and the inner member 244). Alternatively, or additionally, the inner member 244 may be held in place while the outer catheter 240 is retracted proximally. In either case, the sensor assembly 212 can be deployed out of the distal opening 288 with the proximal portion 275 of the sensor 270 retained within the socket 294 of the inner member 244. It will be appreciated that the anchor 274 (not shown) may then be expanded, or will self-expand, upon being deployed from the distal opening 288 of the outer catheter 240.

Figure 8:
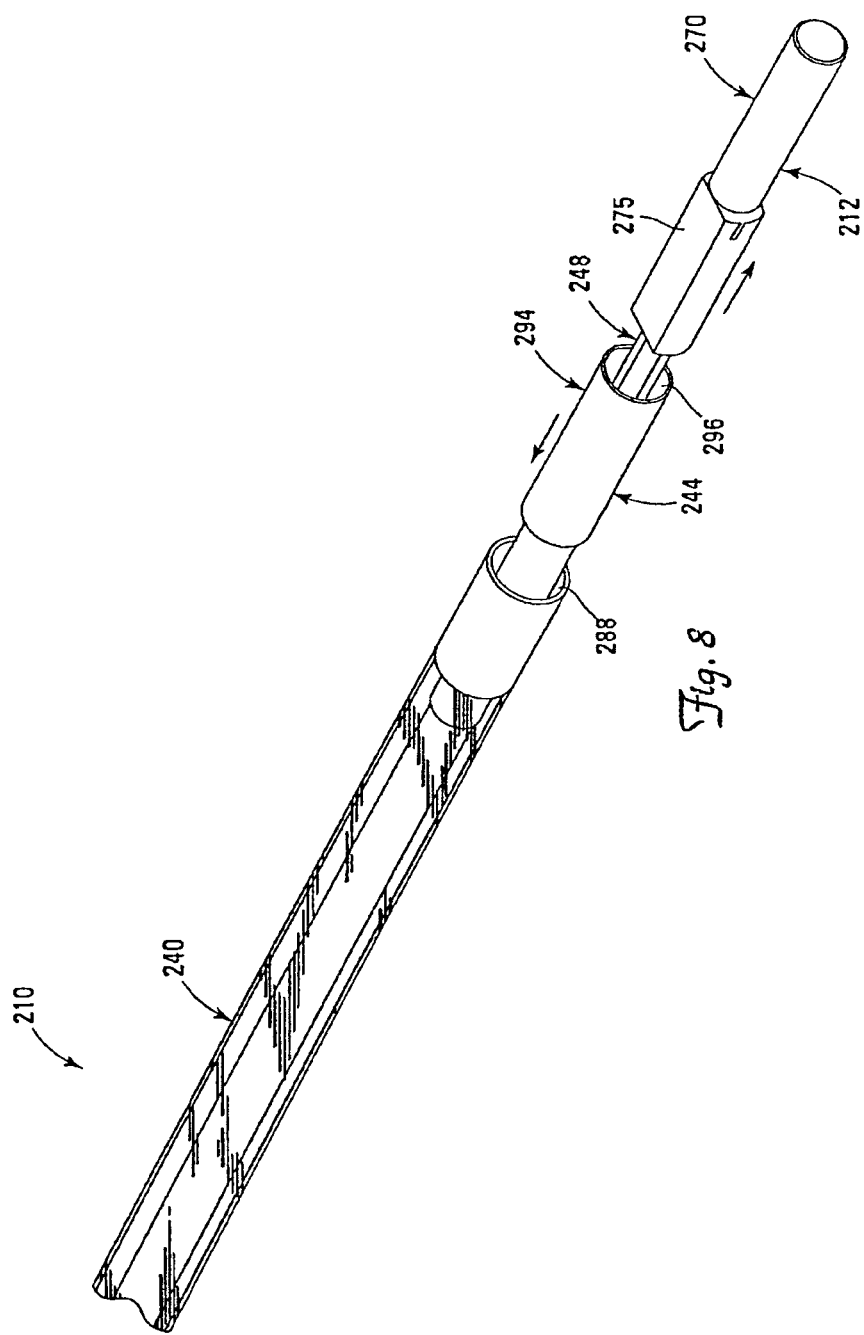
Figure 9:
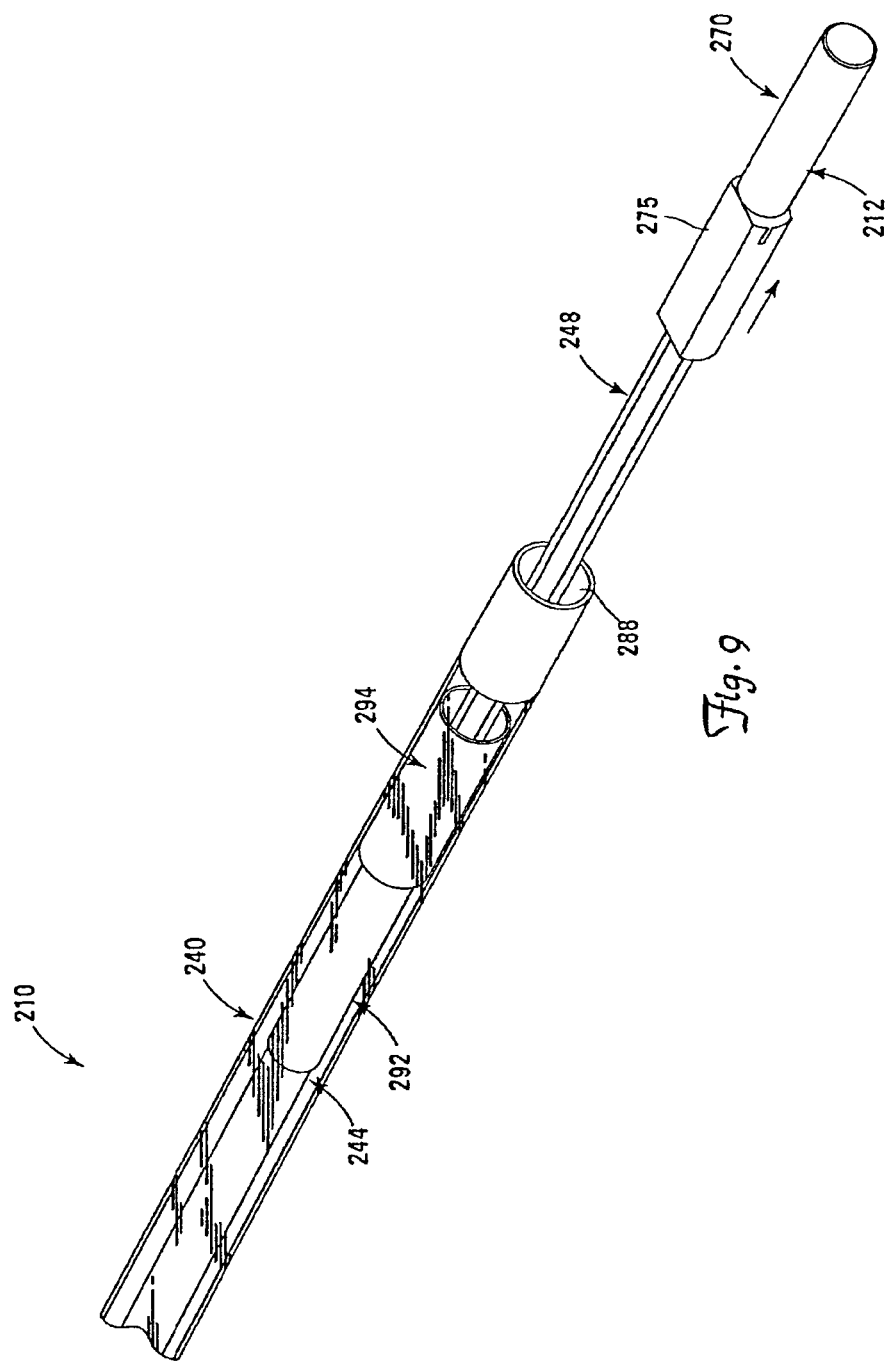

FIGS. 8-9 illustrate the delivery system 210 with the sensor assembly 212 displaced distally from the distal opening 296 of the socket 294, with the retaining element 248 still releasably coupled to the sensor 270. Such displacement can be accomplished, for example, by maintaining the sensor assembly 212 in position using the retaining element 248 and simultaneously retracting the inner member 244 (e.g., by operating a control mechanism such as a thumbwheel, not shown, coupled to the inner member 244). Alternatively, or additionally, and particularly if the anchor (not shown) has not yet significantly engaged with the target vessel tissue, the inner member 244 may be maintained in position while the retaining element 248, and accordingly, the sensor assembly 212, are pushed in the distal direction. As shown in FIG. 9, the inner member 244 can, in some embodiments, be fully retracted within the outer catheter 240 with the retaining element still coupled to the sensor 270.

Figure 10:
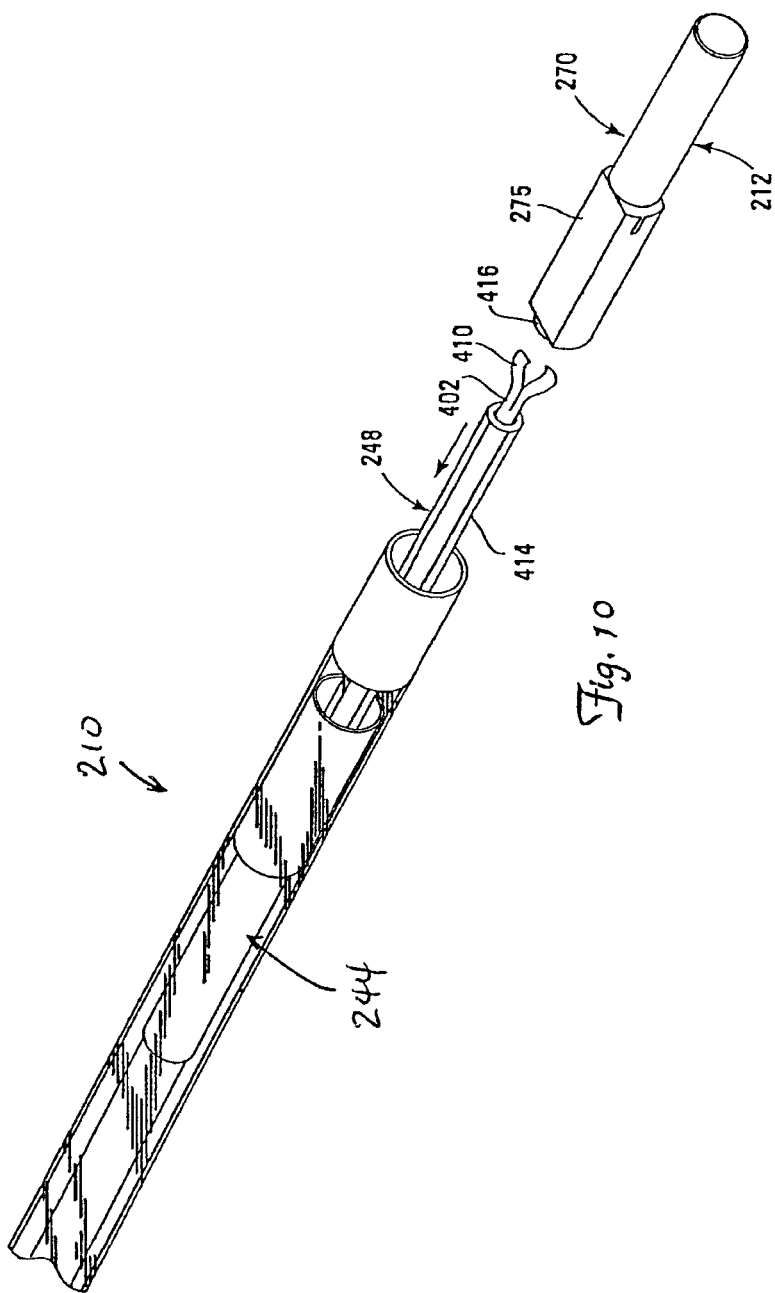

FIG. 10 illustrates the delivery system 210 with the retaining element 248 fully disengaged and de-coupled from the sensor assembly 212 and partially retracted back within the inner member 244 and outer catheter 240. In the illustrated embodiment, the retaining element 248 is shown to be substantially similar to the retaining element 48 above, and includes an inner body member 402 including a plurality of distal jaw members 410, and an outer actuating member 414 disposed over the body member 402 for causing the jaw members 410 to engage the sensor 270. Again, however, any structure or mechanism capable of releasably engaging and retaining the sensor assembly 212 as necessary for the particular deployment technique used can be incorporated into the retaining element 248.

As previously discussed, the outer catheter 240, the inner member 244, and/or the retaining element 248 may, in various embodiments, be of substantially the same or identical construction as the outer catheter 40, the inner member 44, and the retaining element 48 described above. In some embodiments, all or part of the distal end portion 292, including the socket 294, may be of a relatively low durometer material, e.g., low durometer Pebax, as compared to other portions of the inner member 244. Such configurations advantageously promote positive engagement of the sensor proximal end portion 275 within the socket 294, yet still permit the sensor 270 to be released from the socket 294 without requiring undue force.

Figure 11:
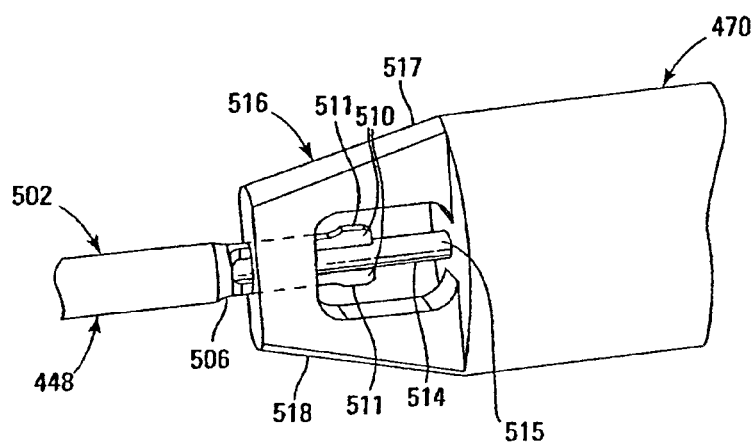
FIGS. 11-13 illustrate a distal portion of an alternative retaining element according to another embodiment of the present invention.
Figure 12:
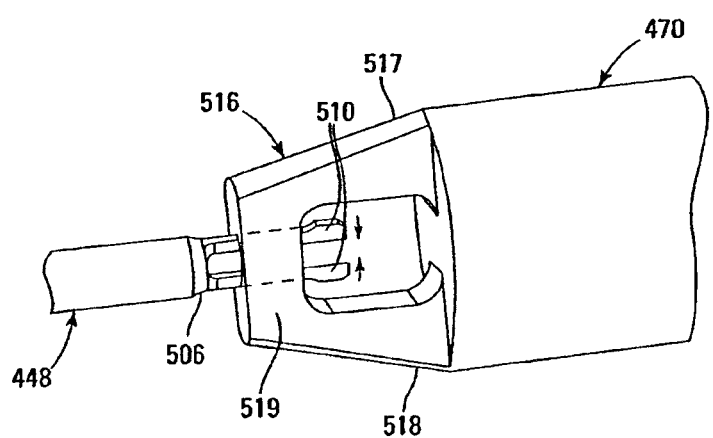
Figure 13:
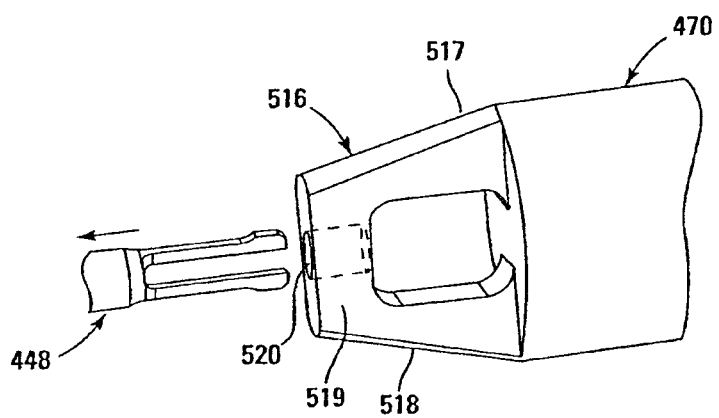

FIGS. 11-13 illustrate a distal portion of an alternative retaining element 448 coupled to a sensor 470 according to another embodiment of the present invention. As shown in FIGS. 11-13, the retaining element 448 includes a generally tubular, elongate body 502 having a distal end 506, a pair of deflectable jaw members 510 extending distally from the distal end 506 and each terminating in a distal tip portion 511, and an actuating member 514 slidably disposed within the body 502 and including a distal end portion 515. As shown, the actuating member 514 is dimensioned such that the distal end portion 515 can be positioned at a location at least proximate the distal tips of the jaw members 510. As can perhaps be best seen in FIGS. 11-12, the jaw members 510 are configured to be radially deflectable (as indicated by the arrows in FIG. 12), and the actuating member 514 operates to prevent such deflection when positioned substantially as shown in FIG. 11. In the illustrated embodiment, the retaining element 448 includes two jaw members 510 positioned approximately 180 degrees apart. In other embodiments, the retaining element 448 may include three or more jaw members 510, which may be substantially equally spaced apart about the circumference of the body 502.

As shown, the jaw members 510 are configured to frictionally engage an engagement feature of the sensor 470 (or other implantable medical device), which engagement feature in the illustrated embodiment is a yoke 516 having a pair of lateral arms 517, 518, and a cross member 519 extending there between. As can perhaps be best seen in FIG. 13, the cross member 519 includes a through aperture 520 for receiving the jaw members 510. The jaw members 510 can be deflected inward to facilitate their insertion through the aperture 520 (as indicated by the arrows in FIG. 12). In the illustrated embodiments, the distal tip portions 511 of the jaw members 510 are chamfered or otherwise radiused to further facilitate their insertion through the aperture 520, although this is not a requirement.

When inserted through the aperture 520 as shown in FIGS. 11-12, the jaw members 510 bear upon and frictionally engage the inner surface of the aperture 520, thus coupling the retaining element 448 to the sensor 470. The distal end portion 515 of the actuating member 514, when inserted through the body 502 to a location at least near the distal tip portions 511 of the jaw members 510, operates to prevent inward deflection of the jaw members 510, thus maintaining positive frictional engagement with the inner surface of the aperture 520. In the illustrated embodiment, the distal tip portions 511 of the jaw members 510 are enlarged to further prevent the jaw members 510 from backing out of the aperture 520.

In other embodiments, the jaw members 510 may normally be biased inwardly (as indicated by the arrows in FIG. 12), and the distal end portion 510 operates, when positioned proximate the distal tip portions 511, to deflect the jaw members 510 outwardly to bear upon the inner surface of the aperture 520.

The dimensions of the retaining element 448 are selected based on the size of the sensor 470 and the delivery system in which the sensor 470 is deployed. In exemplary embodiments, the outer diameter of the body 502 may be from about 0.014 inches to about 0.025 inches, although these sizes are in no way exclusive.

The retaining element 448 and its constituent components may be made from any materials known in the art or later developed for use in guide wires, stylets, and the like. Such materials include any number of biocompatible metals, alloys, composites, and polymeric materials. The jaw members 510 may be made integrally with the body 502, or alternatively, may be attached to the distal end 506 by methods known in the art (e.g., welding, adhesives). In some embodiments, the jaw members 510 may advantageously be made from materials having shape memory and/or superelastic properties, including shape memory polymers and alloys such as Nitinol.

In operation, the jaw members 510 can be inserted through the aperture 520 by deflecting the jaw members 510 inward, with the actuating member 514 located substantially as shown in FIG. 11. Where, for example, the distal tip portions 511 of the jaw members 510 are chamfered, such deflection can be accomplished simply by pushing the jaw members 510 through the aperture 520. In other embodiments, a standard tool (not shown) such as surgical forceps and the like may be used to deflect the jaw members 510 inwardly.

Next, the actuating member 514 may be advanced distally such that the distal end portion 515 is positioned at a location sufficient to prevent inward deflection of the jaw members 510 (see FIG. 11). It will be appreciated that the actuating member 514 need not be advanced fully beyond the jaw members 510 as shown in FIG. 11.

To de-couple the retaining element 448 from the yoke 516, the actuating member 514 can be retracted proximally relative to the body 502 (e.g., by pulling on a proximal end, not shown, of the actuating member 514 while holding the body 502 in position), to a location substantially as shown in FIG. 12. If the sensor 470 is sufficiently secured in place (e.g., by an anchoring device), the body 502 may then be retracted, and the jaw members 510 can deflect inwardly as the body 502 is retracted relative to the sensor 470. Alternatively, a tube or similar structure (not shown) may be positioned over the body 502 to push against the cross member 519 as the body 502 is retracted.

Although the retaining element 448 and the yoke 516 are shown and described as being used to releasably engage an implantable sensor, it is emphasized that they may also advantageously be used in combination with other implantable medical devices (e.g., stents, drug delivery devices, etc.).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An apparatus for releasably engaging an implantable medical device during delivery, the implantable medical device including an engagement feature, the apparatus comprising:
   an elongate, tubular body having an open distal end;
   a plurality of deflectable jaw members coupled to the distal end of the body and extending distally from the distal end of the body and terminating in distal tip portions, the jaw members adapted to releasably engage the engagement feature of the implantable medical device; and
   an actuating member slidably disposed within the body and including a distal end portion operable to prevent inward deflection of the jaw members when positioned proximate the distal tip portions.

2. The apparatus of claim 1 wherein the engagement feature includes an aperture sized to at least partially receive the jaw members and having an inner surface, and wherein the jaw members are adapted to frictionally engage the inner surface.

3. The apparatus of claim 2 wherein the jaw members are adapted to deflect inwardly with respect to the distal end of the body for insertion through the aperture.

4. The apparatus of claim 1 wherein the actuating member is movable within the body and dimensioned to extend distally beyond the distal tip portions of the jaw members.

5. The apparatus of claim 2 wherein the distal tip portions of the jaw members are chamfered to facilitate insertion through the aperture.

6. The apparatus of claim 1 wherein the plurality of jaw members includes a pair of jaw members disposed about 180 degrees apart.

7. The apparatus of claim 1 wherein the plurality of jaw members includes three jaw members disposed about 120 degrees apart.

8. The apparatus of claim 1 wherein the jaw members are normally biased inwardly with respect to the distal end of the body.

9. The apparatus of claim 8 wherein the distal end portion of the actuating member is further operable to force the jaw members outwardly when positioned proximate the distal tip portions.

10. The apparatus of claim 2 wherein the engagement feature includes a yoke having a pair of lateral arms and a cross member extending between the lateral arms, the aperture located in and extending through the cross member, and further wherein the jaw members are dimensioned to extend through the aperture.

11. The apparatus of claim 1 wherein the body is made from a material selected from the group consisting of stainless steel, shape memory polymers, and shape memory alloys.

12. The apparatus of claim 1 wherein the jaw members are made from Nitinol.

13. A system comprising:
   an elongate catheter having an inner lumen;
   an implantable sensor sized to be slidably received within the lumen, the sensor having a proximal portion including an engagement feature; and
   a retaining element movable within the lumen and including:
      an elongate, tubular body having an open distal end;
      a plurality of deflectable jaw members coupled to the distal end of the body and extending distally from the distal end of the body and terminating in distal tip portions, the jaw members adapted to releasably engage the engagement feature of the implantable medical device; and
      an actuating member slidably disposed within the body and including a distal end portion operable to prevent inward deflection of the jaw members when positioned proximate the distal tip portions.

14. The system of claim 13 wherein the sensor is a pressure sensor.

15. The system of claim 14 wherein the catheter is dimensioned to extend transvenously from a percutaneous incision in a patient to a pulmonary artery of the patient.

16. The system of claim 15 wherein the sensor is adapted to sense blood pressure in the pulmonary artery.

17. The system of claim 16 wherein the engagement feature includes an aperture sized to at least partially receive the jaw members and having an inner surface, and wherein the jaw members are adapted to frictionally engage the inner surface.

18. The apparatus of claim 17 wherein the jaw members are adapted to deflect inwardly with respect to the distal end of the body for insertion through the aperture.

19. An apparatus for releasably engaging an implantable medical device during delivery, the apparatus comprising:
   an elongate, tubular body having an open distal end;
   a plurality of deflectable jaw members coupled to the distal end of the body and extending distally from the distal end of the body and terminating in distal tip portions, the jaw members adapted to releasably engage an engagement feature of an implantable medical device;
   an actuating member slidably disposed within the body and including a distal end portion operable to prevent inward deflection of the jaw members when positioned proximate the distal tip portions; and
   the implantable medical device including the engagement feature comprising a pair of lateral arms, a cross member extending between the lateral arms, the cross member defining an aperture that extends through the cross member and allowing the jaw members to at least partially extend through the aperture.

* * * * *